United States Patent [19]

Haas et al.

[11] Patent Number: 5,276,201

[45] Date of Patent: Jan. 4, 1994

[54] PROCESS FOR THE PRODUCTION OF 3-HYDROXYALKANALS

[75] Inventors: Thomas Haas, Frankfurt; Dietrich Arntz, Oberursel; Reinhold Brand, Hanau, all of Fed. Rep. of Germany

[73] Assignee: Degussa Aktiengesellschaft, Frankfurt am Main, Fed. Rep. of Germany

[21] Appl. No.: 981,324

[22] Filed: Nov. 24, 1992

[30] Foreign Application Priority Data

Nov. 27, 1991 [DE] Fed. Rep. of Germany ....... 4138982

[51] Int. Cl.$^5$ .................... C07C 45/61; C07C 45/64
[52] U.S. Cl. .................................... 568/491; 568/496
[58] Field of Search ................... 568/458, 491, 496

[56] References Cited

U.S. PATENT DOCUMENTS

| | | | |
|---|---|---|---|
| 2,434,110 | 1/1948 | Hatch et al. | 568/458 |
| 3,536,763 | 10/1970 | Eleuterio et al. | 568/458 |
| 5,015,789 | 5/1991 | Arutz et al. | 568/862 |

FOREIGN PATENT DOCUMENTS

| | | |
|---|---|---|
| 3926136 | 2/1991 | Fed. Rep. of Germany . |
| 4038192 | 6/1992 | Fed. Rep. of Germany . |
| 1185615 | 3/1970 | United Kingdom . |

Primary Examiner—Werren B. Lone
Attorney, Agent, or Firm—Beveridge, DeGrandi, Weilacher & Young

[57] ABSTRACT

A process for the production of 3-hydroxyalkanals, more particularly 3-hydroxypropionaldehyde, by hydration of the basic 2-alkenals, more particularly acrolein, in the presence of a solid catalyst containing acid functional groups. The catalysts are based on an inorganic support containing basic activity centers (which are at least partly occupied by a polybasic acid, of which the first $pK_s$ value is between 0 and 3, in a form in which it cannot be removed by water) enables the hydration to be carried out with high selectivity. At the same time, the disadvantages of known organic fixed-bed catalysts are avoided. Preferred catalyst are based on pyrogenic titanium dioxide with phosphoric acid fixed thereon.

14 Claims, No Drawings

PROCESS FOR THE PRODUCTION OF 3-HYDROXYALKANALS

Introduction and Background

The present invention relates to a process for the production of 3-hydroxyalkanals containing 3 to 12 carbon atoms, more particularly 3-hydroxypropionaldehyde, by hydration of the basic 2-alkenals with water in heterogeneous phase in the presence of a solid catalyst containing acidic functional groups.

According to U.S. Pat. No. 2,434,110, 2-alkenals corresponding to the general formula $H_2C=CR-CHO$ (in which R is hydrogen or alkyl, more particularly acrolein and methacrolein) can be hydrated with water in the presence of acidic catalysts, with the result that the corresponding 3-hydroxyalkanals are formed. Thus, 3-hydroxypropionaldehyde (HPA) can be obtained from acrolein and, by hydrogenation, propane-1,3-diol is produced which is acquiring increasing significance as a monomer unit for polyesters and polyurethanes.

In the process according to U.S. Pat. No. 2,434,110, acids dissolved homogeneously in the reaction mixture (such as for example sulfuric acid, hydrochloric acid, phosphoric acid, oxalic acid, acidic salts, or acetic acid, sulfuric acid being preferred) are used as the catalysts. The disadvantage of this process lies in the poor selectivities.

Other processes have been developed to improve the selectivity of the hydration of acrolein. Although useful selectivities can be obtained using carbon dioxide as catalyst (see British Patent 1,185,615), the long reaction time required considerably reduces the volume/time yield of the process. Finally, heterogeneous catalysts, namely mildly acidic carboxyfunctional ion exchangers, may also be used (see U.S. Pat. No. 3,536,763). However, it has been found in practice that conventional carboxyfunctional ion exchangers are limited in their effectiveness and hence require long reaction times.

An improvement in the volume/time yield, coupled with high selectivity, was provided by ion exchangers containing phosphonic acid groups (see DE-OS 39 26 136). The disadvantage of processes using ion exchangers based on an organic polymer matrix containing phosphonate groups according to DE-A 39 26 136, and chelating anchor groups according to hitherto unpublished German patent application P 40 38 192.7, lies in the cost of the ion exchangers, in their limited heat resistance, and in the fact that the deactivated ion exchanger cannot be regenerated.

SUMMARY OF THE INVENTION

One object of the present invention was to provide further catalysts for the heterogeneous catalysis which would be readily accessible and, like the special ion exchangers mentioned above, would enable 2-alkenals, particularly acrolein, to be hydrated with high selectivity.

Accordingly, the present invention relates to a process for the production of 3-hydroxyalkanals, containing 3 to 12 carbon atoms, by hydration of the basic 2-alkenals with water in heterogeneous phase in the presence of a solid catalyst containing acidic functional groups. Reaction temperatures for the process can vary widely (e.g., 20° C. to 120° C.). A pressure of 1 bar to 20 bar has been found to be suitable for the process. The initial concentration of the 2-alkenal in the liquid reaction mixture ranges from 3 to 30% by weight. A feature of the process of the invention resides in employing a catalyst made up of an inorganic support having basic activity centers which are at least partly occupied by a polybasic acid, of which the $pK_s$ value of the first dissociation stage is between 0 and 3, in a form in which the polybasic acid cannot be removed by water.

The support material used for purposes of the invention must exhibit adequate stability to the acid which is used for application to the support. Suitable support materials are those which have both acidic and also basic centers, more particularly oxides and mixed oxides. The ratio of the number and strength of the acidic or basic centers should be such that a 10% by weight aqueous suspension of the support powder in water leads to a pH value of 2 to 5 and preferably 3 to 4. Pyrogenic $TiO_2$ is particularly preferred because it has both acidic and also basic centers in a balanced ratio (K. I. Khadzhiivanöv, A. A. Davydov, D. G. Klisurski; Kinetika i Kataliz, 29, 1, 161–167) and the corresponding pH is at 3.5. Highly acidic oxides (for example Al silicates) and highly basic oxides (for example $\gamma$-$Al_2O_3$) are less suitable. The production of pyrogenic $TiO_2$ having these characteristics is known in the art.

A particularly suitable polybasic acid, of which the $pK_s$ value of the first dissociation stage is in the range of 0 to 3, i.e. at +1.96, is phosphoric acid.

The polybasic acid fixed to the inorganic support should not be removed during the hydration process because a purification stage might otherwise be necessary during the further processing of the 3-hydroxyalkanal-containing reaction mixture, in addition to which the useful life of the catalyst would be shortened.

The support and the polybasic acid are matched with one another in such a way that, on the one hand, sufficient acidity is obtained at the surface of the catalyst and, on the other hand, the system acts as an acid/base buffer. The expert can easily determine the necessary coordination between support and acid in a preliminary test.

DETAILED DESCRIPTION OF THE INVENTION

The catalyst according to the invention can be produced by typical impregnation of the inorganic support with an aqueous solution of the polybasic acid, drying, calcination at temperatures above 150° C. (more particularly at 250° to 500° C.), and washing with water until the wash water is free from acid. It is assumed that a firm bond is established between the carrier and the central atom of the acid through an oxygen atom during calcination, for example Ti-O-P in the case of the particularly preferred catalyst based on $TiO_2/H_3PO_4$.

Particularly suitable polybasic acids are oxoacids of the elements phosphorus, arsenic, vanadium, chromium, molybdenum and tungsten. The acids may even be homopolyacids or heteropolyacids of these elements. Acids having a $pK_s$ value for the first association stage below zero are ruled out because they lead to catalysts with inadequate selectivity. Although acids having a first $pK_s$ value above 3 can still be fixed to the supports, selectivity also falls in their case, and the 2-alkenal may polymerize on the catalyst.

2-Alkenal, more particularly acrolein, and water are reacted in the form of a mixture in the presence of the heterogeneous catalyst, the temperature being adjusted so that the liquid phase remains homogeneous. The starting concentration of 2-alkenal in the liquid phase is between 3 and 30% by weight and, more particularly, between 10 and 18% by weight. If desired, polymerization inhibitors (such as for example hydroquinone, hydroquinone monomethyl ether or butylated phenols) may be added in effective quantities to the 2-alkenal/-water mixture. If it is circulated through a catalyst bend, the liquid phase also contains 3-hydroxyalkanal formed and secondary products from the reaction of the 2-alkenal or derivatives of the 3-hydroxyalkanal formed. The hydration may be carried out over a wide range of temperatures, the preferred reaction temperature being between 50° C. and 90° C. The reaction is typically carried out under normal pressure or only moderate pressure.

The hydration may be carried out discontinuously or continuously using reactors know per se, such as for example stirred reactors, loop reactors, suspended bed reactors, fluidized bed reactors, and flow tube reactors, all of which are known in the art. Reactors operating on the principle of the flow tube are preferred to loop and stirred reactors. The throughflow rate through a flow tube, which contains the heterogeneous acidic catalyst according to the invention and which is provided with a heatable jacket, and also the reaction temperature will be adjusted so that the required acrolein conversion is achieved. The LHSV (liquid hourly space velocity) value is typically between 0.1 and 2 $h^{-1}$ and, preferably more than 0.5 $h^{-1}$. The reaction mixture can also be passed repeatedly through the catalyst bed providing relatively large dead volumes, in which the reaction mixture is present at the reaction temperature in the absence of the hydration catalyst, are avoided.

After removal of the heterogeneous catalyst, which is normally carried out by sedimentation or filtration or, where fittings known per se for fixed-bed catalysts are used, takes place almost automatically, the reaction mixture is freed from unreacted acrolein, if necessary.

For an acrolein conversion of 30 to 80%, this measure will always be recommendable because acrolein can be directly returned to the process, even if it has been removed as water-containing acrolein. The acrolein may be removed in a manner known in the art by distillation, preferably under reduced pressure and at temperatures below 80° C. It is particularly favorable to feed the reaction mixture to a thin-layer evaporator in which both unreacted acrolein and also part of the water present in the reaction mixture are distilled off together under mild conditions. In this way, a concentrated aqueous solution of 3-hydroxyalkanal is obtained as the bottom product which has an advantageous effect on the further processing of the reaction mixture and the energy consumption of the process.

As already mentioned, the reaction mixture containing 3-hydroxyalkanal, after removal of the unreacted 2-alkenal, is generally subjected as such to the reaction leading to secondary products, more particularly to hydrogenation, without the 3-hydroxyalkanal having to be isolated beforehand.

The catalytic hydrogenation of, for example, 3-hydroxypropionaldehyde to propane-1,3-diol in the liquid phase is carried out in a known manner and in typical hydrogenation reactors (known in the art). The catalyst may be present in suspended form per se or may be fixed to a support or may be a part of fixed-bed catalysts. Homogeneous catalysts may also be used. Particularly suitable suspension catalysts are Raney nickel, which may be doped with various other catalytically active metals, and platinum on active carbon and other carriers. Among the fixed-bed catalysts, the substances mentioned, for example in U.S. Pat. No. 2,434,110 (which is incorporated by reference), are used, nickel catalyst having proved to be particularly effective catalysts.

A high volume/time yield is obtained in the hydrogenation stage if the solution to be hydrogenated has a pH value of 2.5 to 6.5, and preferably around 6, and if the hydrogenation temperature is in the range from 25° to 100° C.

The new catalysts are an addition to the range of effective hydration catalysts. Accordingly, selectivities above 70% can easily be obtained. The supports for the new catalysts and the polybasic acids are readily accessible, in addition to which the production of the catalysts does not involve any difficulties. It could not be foreseen that the catalyst found in accordance with the invention would show the necessary activity and would have a long useful life which has a favorable effect on the economy of hydration of the 2-alkenals.

In contrast to the use of acidic ion exchangers based on an organic polymer matrix as heterogeneous catalysts, the catalysts according to the invention based on inorganic supports can be unexpectedly operated at relatively high reaction temperatures without any danger of irreversible damage. The catalyst and/or reactor costs can be reduced by relatively high reaction temperatures. In addition, deactivated catalysts based on inorganic supports can be regenerated, for example by burning off or oxidation of the carbon-containing deposits and, if necessary, replacement of the polybasic acid, which is not possible with catalysts based on an organic polymer matrix.

EXAMPLES 1 AND 2 AND COMPARISON EXAMPLES CE1 AND CE2

The following test is carried out to determine the activity and selectivity of the catalysts according to the invention:

A 50 ml Septum flask is filled with 25 ml catalyst and water is added in such a quantity that the catalyst is just covered. 1.6 g water and acrolein (Ac) are also added so that an Ac concentration in the aqueous phase of approximately 18% by weight is established. The mixture is shaken by rotation for 3 minutes at room temperature and the actual acrolein concentration of a sample is determined by gas chromatography. The sample is then shaken for a certain reaction time in a water bath at the temperature indicated and subsequently analyzed. Table 1 shows particulars of the support and the acid fixed thereto, the conversion, the selectivity after the indicated reaction time, the starting concentration of acrolein, and the reaction temperature.

See Example 5 for production of the catalysts.

TABLE 1

| Example No. or Comparision Example No. | Catalyst | | Starting acrolein concentration (% by weight) | Hydration | | | |
|---|---|---|---|---|---|---|---|
| | | | | Reaction | | | |
| | Support | Acid | | Temp. (°C.) | Time (h) | Conversion (%) | Selectivity (%) |
| 1 | TiO$_2$ | H$_3$PO$_4$ | 18.5 | 70 | 1 | 42 | 81 |

TABLE 1-continued

| Example No. or Comparision Example No. | Catalyst Support | Catalyst Acid | Starting acrolein concentration (% by weight) | Hydration Reaction Temp. (°C.) | Hydration Reaction Time (h) | Conversion (%) | Selectivity (%) |
| --- | --- | --- | --- | --- | --- | --- | --- |
| CE1 | $TiO_2$ | $NaH_2PO_4$ | 19.0 | 70 | 1 | 41 | 50 |
| 2 | gramma-$Al_2O_3$ | $H_3PO_4$ | 17.0 | 50 | 6.5 | 58 | 71.4 |
| CE2 | gramma-$Al_2O_3$ | $NaH_2PO_4$ | 16.0 | 70 | 1 | 91 | 3 |

EXAMPLE 3

In a laboratory fixed-bed reactor with $TiO_2$ impregnated with phosphoric acid as catalyst, the hydration of acrolein is carried out continuously over a prolonged period. The conversion and selectivity are determined by analysis of the product solution.

The reactor consists of a graduated, coolable 2 liter glass vessel for the aqueous acrolein starting solution, and HPLC pump for the transport of the reaction mixture, a thermostatically controlled, pressure-resistant, precision-ground glass tube (300 mm×26 mm), which accommodates the catalyst filling and which is closed at both ends by adjustable screw caps, a pressure-retaining valve and a 2 liter glass receiver cooled to +5° C. for the product solution and the necessary temperature control systems.

The acrolein/water mixture is introduced first and, by means of the HPLC pump, is pumped at a constant rate through the fixed bed of 138 ml catalyst kept at the reaction temperature. After a startup time of 3 to 5 h to establish steady-state conditions and after the receiver has been changed, acrolein solution is pumped through the thermostatically controlled glass tube over a period of several hundred hours under constant test conditions. The product solution is analyzed at certain time intervals (approximately every 48 h).

| | |
| --- | --- |
| Catalyst used: | Phosphoric-acid-impregnated $TiO_2$ (according to Example 5) |
| Starting acrolein concentration: | 16.5% by weight |
| Reaction temperature: | 50–70° C. |
| LHSV (liquid hourly space velocity): | 0.5 $h^{-1}$ |

The total duration of the test was 900 h. During this time, the conversion was kept at 50%±2%. The temperature was increased from 50° C. to 70° C. during the test to keep the conversion constant. The selectivity of the reaction was 81%±2%.

After a test duration of 900 h, no phosphorus could be detected in the product solution obtained (detection limit 1 mg/l). The phosphorus content of the catalyst after 900 h was 2000 ppm.

After the 900 h test, the reaction temperature was increased to 100° C. and the test was continued at an LHSV value of 0.5 $h^{-1}$. Even under these conditions, the phosphorus content in the solution was below the detection limit.

EXAMPLE 4

Hydrogenation of an aqueous solution of 3-hydroxypropionaldehyde (HPA) obtained in accordance with Example 3.

The reaction solution of Example 3 is freed from unreacted acrolein in a distillation column at 500 mbar. In a 1000 ml autoclave equipped with an aerating stirrer, 500 g of the 8.7% HPA solution are hydrogenated for 2 h in the presence of 5 g Raney nickel, the reaction being carried out under a hydrogen pressure of 135 bar, at a reaction temperature of 60° C., at a stirrer speed of 1000 r.p.m., and at a pH value of 4. The HPA conversion was 99.9% and the yield of propane-1,3-diol, based on the HPA used, was 99.8%.

EXAMPLE 5

Production of the catalysts used in Examples 1 and 2 and in Comparison Examples CE1 and CE2:

200 g support (gamma-aluminum oxide or pyrogenic titanium dioxide having a specific BET surface of 50 $m^2/g$) are left standing for 12 h in 20% by weight aqueous $H_3PO_4$ or $NaH_2PO_4$ solution. The supports thus impregnated are dried for 4 h at 150° and subsequently calcined for 1 h at 450° C. The catalysts thus produced are washed with water at 80° C. until the washing water is acid-free.

Further variations and modifications of the invention will become apparent to those skilled in the art from the foregoing and are intended to be encompassed by the claims appended hereto.

German Priority Application P 41 38 982.4, filed Nov. 27, 1991, is relied on and incorporated by reference.

What is claimed:

1. A process for the production of 3-hydroxyalkanals containing 3 to 12 carbon atoms, comprising hydrating the basic 2-alkenals with water in heterogeneous phase in the presence of a solid catalyst containing acidic functional groups at a reaction temperature of 20° C. to 120° C., under a pressure of 1 bar to 20 bar and with a initial concentration of the 2-alkenal in the liquid reaction mixture of to 30% by weight; wherein said catalyst comprises an inorganic support having basic activity centers which are at least partly occupied by a polybasic acid, of which the first $pK_s$ value is between 0 and 3, in a form in which said polybasic acid cannot be removed by water.

2. The process according to claim 1, wherein said inorganic support is titanium dioxide.

3. The process according to claim 2, wherein said inorganic support is pyrogenically produced titanium dioxide.

4. The process according to claim 1, wherein said polybasic acid is selected from the group consisting of oxoacids of the elements phosphorus, arsenic, vanadium, chromium, molybdenum and tungsten.

5. The process according to claim 4, wherein said polybasic acid is phosphoric acid.

6. The process according to claim 1, wherein said 2-alkenal is acrolein.

7. The process according to claim 1, wherein said reaction temperature is in the range from 50° C. to 90° C.

8. The process according to claim 1, wherein said concentration of 2-alkenal is between 6 and 20% by weight.

9. The process according to claim 8, wherein said concentration of 2-alkenal is between 10 and 18% by weight.

10. The process according to claim 1, wherein said catalyst is arranged in a fixed bed and said hydrating is carried out by passing the aqueous reaction mixture containing 2-alkenal over said catalyst at LHSV value of 0.1 to 2 h$^{-1}$.

11. The process according to claim 10, wherein said LHSV value is 0.6 to 1.5 h$^{-1}$.

12. The process according to claim 1, further comprising adding polymerization inhibitors selected from the group consisting of hydroquinone, hydroquinone monomethyl ether and butylated phenols.

13. The process according to claim 1, wherein said catalyst is produced by a process comprising impregnating said inorganic support with said polybasic acid, drying to produced a dried product, calcining said dried product at 250° to 500° C. to produce a calcined product, and washing said calcined product with water until said water is acid-free.

14. A process for the production of 3-hydroxyalkanals containing 3 to 12 carbon atoms, comprising hydrating the basic 2-alkenals with water in heterogeneous phase in the presence of a solid catalyst containing acidic functional groups at a reaction temperature of 20° C. to 120° C., under a pressure of 1 bar to 20 bar and with an initial concentration of the 2-alkenal in the liquid reaction mixture of 3 to 30% by weight; wherein said catalyst comprises an inorganic support having basic activity centers which are at least partly occupied by a polybasic acid, of which the first $pK_s$ value is between 0 and 3, in a form in which said polybasic acid cannot be removed by water, wherein said polybasic acid is selected from the group consisting of oxoacids of the elements phosphorus, arsenic, vanadium, chromium, molybdenum and tungsten, and wherein said inorganic support is titanium dioxide or gamma-aluminum oxide.

* * * * *